United States Patent

Payzant

[11] Patent Number: 5,846,305
[45] Date of Patent: Dec. 8, 1998

[54] LIQUID WOOD PRESERVATIVE SOLUTION

[75] Inventor: John Payzant, Edmonton, Canada

[73] Assignee: Michael Wall & Sons Enterprises Ltd., Spruce Grove, Canada

[21] Appl. No.: 736,323

[22] Filed: Oct. 23, 1996

Related U.S. Application Data

[60] Provisional application No. 60/009,831 Jan. 16, 1996.
[51] Int. Cl.$^6$ .......................... A01N 59/14; A01N 59/20
[52] U.S. Cl. ................. 106/18.3; 106/18.32; 424/630; 424/638; 424/657; 514/499; 514/500
[58] Field of Search ................. 106/18.3, 18.32; 424/630, 638, 657; 514/499, 500

[56] References Cited

U.S. PATENT DOCUMENTS

| | | | |
|---|---|---|---|
| 4,269,875 | 5/1981 | Bechgaard et al. | 427/291 |
| 4,461,721 | 7/1984 | Goettsche et al. | 106/18.3 |
| 4,610,881 | 9/1986 | Bechgaard | 424/657 |
| 4,731,297 | 3/1988 | Makus et al. | 428/35 |
| 5,084,280 | 1/1992 | West | 424/658 |
| 5,207,823 | 5/1993 | Shiozawa et al. | 106/18.3 |
| 5,304,237 | 4/1994 | Barth et al. | 106/18.3 |
| 5,342,438 | 8/1994 | West | 106/18.3 |
| 5,478,598 | 12/1995 | Shiozawa | 106/18.3 |
| 5,525,147 | 6/1996 | Dunstan et al. | 106/18.3 |

*Primary Examiner*—Anthony Green
*Attorney, Agent, or Firm*—Davis and Bujold

[57] ABSTRACT

A liquid wood preservative solution includes sufficient quantities of a copper compound known as having beneficial effects as a wood preservative to provide a copper metal content of between 1% and 6% by weight. At least 6% by weight of a liquid amine solvent is provided for every 1% of the copper metal. The liquid wood preservative solution includes between 10% and 30% by weight of a boron compound known as having beneficial effects as a wood preservative. At least 1% by weight of glycol is provided for every 1% of the boron compound.

6 Claims, No Drawings

LIQUID WOOD PRESERVATIVE SOLUTION

This Application claims the benefit of U.S. Provisional application Ser. No. 60/009,831 filed Jan. 16th, 1996.

FIELD OF THE INVENTION

The present invention relates to a liquid wood preservative solution containing a mixture of copper compounds and boron compounds.

BACKGROUND OF THE INVENTION

Copper compounds are commonly used in wood preservative formulations. An example of such a wood preservative formulation is copper naphthanate diluted in a compatible solvent, such a fuel oil. Boron compounds are also commonly used in wood preservative formulations. An example of such a wood preservative is a boron compound diluted in a compatible solvent, such as propylene glycol. It is well known in the art that a mixture of copper compounds and boron compounds is more effective than either one of these agents alone. Copper compounds and boron compounds have been successfully combined to form a thick paste-like wood preservative formulation. The use of such wood preservative formulation is limited, as it is too viscous to provide anything more than superficial penetration into the wood. A preferred method of applying wood preservative to wood poles is taught in U.S. Pat. No. 4,731,267 which issued to Makus and Bennett in 1988. According to the teachings of this patent, it is preferable to wrap a pad which is saturated in a liquid wood preservative solution around a base of a pole.

A preferred wood preservative would be in the form of a liquid solution that combines a copper compound known as having beneficial effects as a wood preservative and a boron compound known as having beneficial effects as a wood preservative. Unfortunately, copper compounds have limited solubility in solvents known to dissolve boron compounds. This results in a liquid solution that will only remain stable for a matter of a few days. For example, a wood preservative formulation can be prepared containing copper naphthanate diluted in fuel oil and a boron compound diluted in propylene glycol. However, when a pad is saturated with the wood preservative solution in accordance with the teachings of Makus and Bennett, this mixture separates within a few days into a two liquid phase mixture, with one liquid floating above the other. This results in copper naphthanate being applied to one circumferential area of the wood pole and the boron compound being applied to another circumferential area; rather than the desired simultaneous application of a mixture of the two.

SUMMARY OF THE INVENTION

What is required is a stable liquid wood preservative solution which includes a copper compound and a boron compound.

According to the present invention there is provided a liquid wood preservative solution which includes sufficient quantities of a copper compound known as having beneficial effects as a wood preservative to provide a copper metal content of between 1% and 6% by weight. At least 6% of a liquid amine solvent by weight is provided for every 1% of the copper metal. The liquid wood preservative solution includes between 10% and 30% by weight of a boron compound known as having beneficial effects as a wood preservative. At least 1% by weight of glycol is provided for every 1% of the boron compound.

The liquid wood preservative solution, as described above, has proven to be stable substantially homogeneous solution. The solution contains some fine brown particulate impurities, but these do not adversely effect its intended purpose. The preferred copper compound is copper naphthanate and the preferred boron compound is sold by U.S. Borax Inc. under the trademark TIM-BOR. These compounds are preferred due to their known beneficial properties as wood preservatives. The preferred liquid amine solvent is triethanol amine. This amine is preferred as it is much less flammable and doesn't present the same skin sensitivity problems as alternative amines, such as ethanol amine. Triethanol amine so mild that it is commonly used in personal care products, such as shampoo. As copper naphthanate is increased, the amount of triethanol amine must be increased proportionately in order to avoid separation into two liquid phases. Care must be taken not to increase the amount of copper naphthanate nor the amount of boron compound over the recommended maximum percentage range or the mixture will become too viscous for the intended application. Glycol is a solvent known to be compatible with boron compounds. The use of amines enhances the solubility of copper in glycol. It is preferred that propylene glycol be used. Propylene glycol is digestible; as compared to alternative glycols, such as ethylene glycol, which is toxic.

DETAILED DESCRIPTION OF THE PREFERRED EMBODIMENT

The preferred liquid wood preservative solution will now be described. A liquid wood preservative solution in accordance with the teachings of the present invention includes sufficient quantities of a copper compound known as having beneficial effects as a wood preservative to provide a copper metal content of between 1% and 6% by weight. At least 6% by weight of a liquid amine solvent is provided for every 1% of the copper metal. The liquid wood preservative solution includes between 10% and 30% by weight of a boron compound known as having beneficial effects as a wood preservative. At least 1% by weight of glycol is provided for every 1% of the boron compound.

The formulation which will hereinafter be described represents the preferred formulation. The preferred formulation includes sufficient quantities of copper naphthanate to provide a copper metal content of between 2% and 3% by weight. At least 6% by weight of triethanol amine solvent is provided for every 1% of the copper metal. The preferred formulation includes between 15% and 25% by weight of a boron compound known as having beneficial effects as a wood preservative. At least 1% by weight of propylene glycol is provided for every 1% of the boron compound.

Although various copper compounds can be used, it is preferred that the copper compound be copper naphthanate. Copper naphthanate is viewed as being one of the most effective of the copper compounds used as wood preservatives. A copper metal content of below 1% is not considered to provide a sufficiently effective wood preservative. A copper metal content of between 2% and 3% is considered to be adequate for the intended purpose. Quantities greater than 3% are considered to be redundant. As much as 6% can be included in a formulation, but in order to increase the copper metal percentage above 3% the percentage of other ingredients in the formulation must be reduced which is considered undesirable. One skilled in the art will appreciate the quantity of copper naphthanate that must be used in order to yield a copper metal content of 3%.

Although various boron compounds can be used, it is preferred that the boron compound be one sold by U.S.

Borax Inc. under the trademark TIM-BOR. TIM-BOR is one of the most effective of the boron compounds used as wood preservatives, as it contains a greater proportion of boron by weight. The manufacturer indicates that TIM-BOR is Na2B8O134H2O or Na2O.4B2O3.4H2O. TIM-BOR will have some beneficial effects in a broad range between 10% and 30% by weight. In quantities of less than 10%, the boron content does not provide a sufficiently effective wood preservative. The preferred range is between 15% and 25%, with an ideal formulation at around 20%. If the TIM-BOR is present in quantities exceeding 30%, there is a danger that the boron will make the formulation too viscous. It is not uncommon for pastes to have a boron content of 40%.

Glycol is present in the liquid wood preservative solution, due to its known properties as a solvent compatible with boron compounds. Although various glycols can be used, it is preferred that propylene glycol be used. Propylene glycol is selected will not be harmful to the environment nor to the persons who will be working with the liquid wood preservative solution. It is preferred that there be at least 1% propylene glycol for every 1% of boron compound.

An amine solvent is present in the liquid wood preservative composition, as the presence of the amine solvent enhances the solubility of copper in glycol. The preferred liquid amine solvent is triethanol amine. This amine is preferred as it is much less flammable and doesn't present the same skin sensitivity problems as alternative amines, such as ethanol amine. Triethanol amine is so mild that it is commonly used in personal care products, such as shampoo. In order to ensure the copper naphthanate does not separate there must be at least 6% triethanol amine for every 1% of copper metal.

The following is an example of a formulation that was mixed and left stand for over a year with no visible signs of separation:

| Triethanol amine (85%) | 16.9% |
| --- | --- |
| Propylene Glycol | 37.0% |
| TIM-BOR | 20.1% |
| Copper napthanate (8% copper) with propylene glycol | 26.0 (2% copper) |

Any copper compound which will dissolve in the mixture to form a homogeneous solution is believed to work, but a major concern is cost. Copper naphthanates are preferred because of low cost and an extensive history of usage as an effective wood preservative. Naphthentic acids are a complex mixture of carboxylic acids isolated from petroleum. It is believed that any other copper salt of a carboxylic acid derived from any other source would work just as well. For example, the carboxylic acids resulting from the saponification of vegetable oils and animal fats are, accordingly, believed to work just as well as the naphthenic acids from petroleum. These materials differ mainly in the details of the structure of the organic shrubbery which is appended to the carboxyl group. Copper naphtanates, copper compounds derived from vegetable oils or animal fats, copper compounds derived from aliphatic or aromatic carboxylic acids having 1 to 25 carbon atoms, copper compounds derived from aliphatic or aromatic sulfonates or sulfates having 1 to 25 carbon atoms, and copper salts of inorganic anions such as halides and various sulphur oxides or mixtures of these inorganic compounds with the organic compounds listed above may be used as the copper compound.

It will be apparent to one skilled in the art that modifications may be made to the illustrated embodiment without departing from the spirit and scope of the invention as hereinafter defined in the Claims.

The embodiment of the invention in which an exclusive property or privilege is claimed are defined as follows:

1. A liquid wood preservative solution, comprising:

a homogeneous solution, containing:
sufficient quantities of a copper compound known as having beneficial effects as a wood preservative to provide a copper metal content of between 1% and 6% by weight;
at least 6% by weight of liquid amine solvent for every 1% of the copper metal; between 10% and 30% by weight of a boron compound known as having beneficial effects as a wood preservative; and
at least 1% by weight of glycol for every 1% of the boron compound, such that the homogeneous solution does not separate into liquid layers with the passage of a period time of at least one year.

2. The liquid wood preservative solution as defined in claim 1, wherein the liquid amine solvent is triethanol amine.

3. The liquid wood preservative solution as defined in claim 1, wherein the copper compound is copper naphthanate.

4. The liquid wood preservative solution as defined in claim 1, wherein the glycol is propylene glycol.

5. A liquid wood preservative solution, comprising:

a homogeneous solution, containing:
sufficient quantities of copper naphthanate to provide a copper metal content of between 1% and 6% by weight;
at least 6% by weight of triethanol amine solvent for every 1% of the copper metal;
between 10% and 30% by weight of a boron compound known as having beneficial effects as a wood preservative; and
at least 1% by weight of propylene glycol for every 1% of the boron compound, such that the homogeneous solution does not separate into liquid layers with the passage of a period time of at least one year.

6. A liquid wood preservative solution, comprising:

a homogeneous solution, containing:
sufficient quantities of copper naphthanate to provide a copper metal content of between 2% and 3% by weight;
at least 6% by weight of triethanol amine solvent for every 1% of the copper metal;
between 15% and 25% by weight of a boron compound containing sodium known as having beneficial effects as a wood preservative; and
at least 1% by weight of propylene glycol for every 1% of the boron compound, such that the homogeneous solution does not separate into liquid layers with the passage of a period time of at least one year.

* * * * *